United States Patent [19]

Denyer et al.

[11] Patent Number: 4,457,818

[45] Date of Patent: Jul. 3, 1984

[54] DENTAL COMPOSITIONS FROM URETHANE ACRYLATE, DIACRYLATE MONOMER, CAMPHORQUINONE AND DIMETHYLAMINOETHYL METHACRYLATE

[75] Inventors: Robert Denyer, Macclesfield; Michael S. Fortuin, Middlesbrough, both of England

[73] Assignee: Imperial Chemical Industries PLC, London, England

[21] Appl. No.: 100,039

[22] Filed: Dec. 4, 1979

[30] Foreign Application Priority Data

Dec. 18, 1978 [GB] United Kingdom .............. 48967/78
Apr. 4, 1979 [GB] United Kingdom ................. 7911709

[51] Int. Cl.$^3$ ............................. A61K 5/02; C08F 2/50
[52] U.S. Cl. ......................... 204/159.19; 204/159.23; 525/920; 526/301
[58] Field of Search .................................. 204/159.19

[56] References Cited

U.S. PATENT DOCUMENTS 4,071,424 1/1978 Dart et al. .................... 204/159.19
4,089,763 5/1978 Dart et al. .................... 204/159.18

FOREIGN PATENT DOCUMENTS 1498421 1/1978 United Kingdom .

Primary Examiner—John C. Bleutge
Assistant Examiner—A. H. Koeckert
Attorney, Agent, or Firm—Cushman, Darby & Cushman

[57] ABSTRACT

The invention relates to a dental composition which is suitable as a fissure sealant, dental glaze, bonding agent or orthodontic adhesive and which is a mixture of a selected vinyl urethane prepolymer, selected comonomer, and visible light cure catalyst comprising an organic amine and selected α-diketone.

1 Claim, No Drawings

DENTAL COMPOSITIONS FROM URETHANE ACRYLATE, DIACRYLATE MONOMER, CAMPHORQUINONE AND DIMETHYLAMINOETHYL METHACRYLATE

This invention relates to dental compositions and in particular to liquid dental fissure sealant compositions. Within such fissure sealant compositions are also included dental glaze, bonding agent and orthodontic adhesive compositions.

British patent specification No. 1,352,063 describes vinyl urethane prepolymers which may be mixed with ethylenically unsaturated monomers and polymerised optionally with the inclusion of particulate or fibrous filler reinforcement to produce strong polymeric materials and shaped articles such as tanks, panels, pipes and furniture.

British specification No. 1,408, 265 describes photopolymerisable compositions in which photosensitisers include inter alia α-diketones and reducing agents include inter alia organic amines. British patent specifications nos. 1,465,897 and 1,498,421 describe the use of vinyl urethane prepolymer and at least 50% by weight of certain particulate fillers optionally mixed together with ethylenically unsaturated monomer as dental filling compositions.

It has now been found that selected mixtures of vinyl urethane prepolymers and ethylenically unsaturated monomers have particularly suitable combination of viscosity and surface tension to satisfy requirements for dental fissure sealant applications. For these it is necessary for the surface tension and contact angle on the etched enamel to be low so that the composition in an unpolymerised state flows over an etched tooth surface and into fissures whilst the viscosity should not be so low as to run off the tooth into the patient's mouth. The composition should also have a short setting time (provided that this is not so short as to prevent flow) so that the patient and dentist have maximum comfort and effectiveness during treatment.

According to the present invention a liquid dental composition is provided which comprises (A) a polymerisable vinyl urethane prepolymer which is the reaction product of a urethane prepolymer and an ethylenically unsaturated monomer which is reactive with the urethane prepolymer, (B) 50% to 150% by weight of A of a liquid glycol diacrylate or methacrylate and a photosensitive catalyst which comprises (C) 0.25 to 0.75 parts by weight per 100 parts by weight of A+B of at least one organic amine and (D) 0.3 to 1.0 parts by weight per 100 parts by weight of A+B of at least one α-diketone which is a norbornane dione including substituted derivatives thereof.

The urethane prepolymer is linear, carries isocyanate end groups, and is formed by reaction of a diol with diisocyanate to yield urethane prepolymer having the structure $$OCN-(R_1-NH-CO-O-R_2-O-OC-NH-)_nR_1NCO \quad I$$

where the diisocyanate has the structure OCN—R$_1$—NCO and the diol has the structure HO—R$_2$—OH, wherein R$_1$ is a divalent hydrocarbyl group as hereinafter defined, n is an integer, and R$_2$ is the residue of a condensate of an alkylene oxide with a compound containing two phenolic groups or the residue of an alkylene glycol.

Reaction of the urethane propolymer with the ethylenically unsaturated monomer as defined below yields a polymerisable vinyl urethane prepolymer (A) having the structure

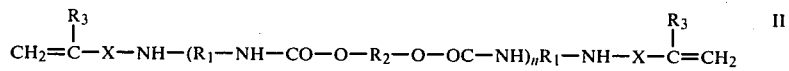

where X is a divalent radical and R$_3$ is hydrogen or a methyl group.

In order that the urethane prepolymer may have isocyanate end-groups it will be appreciated that a molar excess of the diisocyanate over the diol must be used in the preparation of the prepolymer, the value of n in the prepolymer depending on the molar proportion of the diisocyanate to diol used, the value of n decreasing as this latter ratio increases.

Formation of the isocyanate-ended prepolymer may be assisted by the use of catalysts known in the art to assist polyurethane formation, for example, tertiary amines and metal salts, e.g. stannous octoate and in particular dibutyl tin dilaurate.

For reasons of ease of preparation of the urethane prepolymer, the consequently the polymerisable prepolymer, the value of n in the urethane prepolymer is preferably not greater than 10 and is more preferably not greater than 5, that is, the molar ratio of isocyanate groups in the diisocyanate or mixture thereof to hydroxyl groups in the diol or mixture thereof from which the isocyanate-ended prepolymer is produced is preferably 1.1:1 or greater, and more preferably 1.2:1 or greater.

Most suitably, the value of n in the urethane prepolymer is not greater than 3, that is, the molar ratio of isocyanate groups in the diisocyanate or mixture thereof to hydroxyl groups in the diol or mixture thereof from which the urethane prepolymer is produced is suitable 1.33:1 or greater.

Particularly preferred diols are diols of the structure

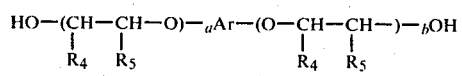

that is oxyalkylated derivatives of phenolic compounds, where R$_4$ and R$_5$ are hydrogen atoms or alkyl groups, e.g. methyl, and Ar is a divalent aromatic group in which each free valency is on an aromatic carbon atom, and in which a+b together preferably total not more than 8 and a is preferably not greater than b+3.

In this case the divalent group R$_2$, has the structure

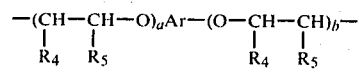

Ar may be mononuclear, e.g. as in phenylene, fused polynuclear as in naphthalene or anthracene, or preferably has the structure

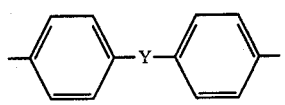

in which Y is a divalent link e.g. —O—, —SO$_2$—, —CO—, or —CH$_2$ or substituted derivative of —CH$_2$ e.g.

Suitably one of the groups R$_4$ and R$_5$ is hydrogen and the other is methyl, or both R$_4$ and R$_5$ are hydrogen, that is, the diol may be prepared by reaction of propylene oxide or ethylene oxide or a mixture thereof with a phenolic compound having the structure

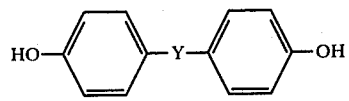

Preferably a plus b is not greater than 4.

Examples of diols which are also suitable include, for example, ethylene glycol and propylene glycol, in in which case R$_2$ has the structure —CH$_2$—CH$_2$ or

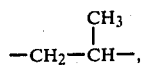

butylene gylcol, diethylene glycol and derivatives thereof in which one or more of the carbon atoms are substituted by atoms or groups which are unreactive towards hydroxyl and isocyanate group.

In the urethane prepolymer I, in at least 80% of the units, the divalent hydrocarbyl group is aliphatic and containing four to eight carbon atoms inclusive, e.g. tetramethylene, pentamethylene, cyclohexyl and branched polymethylene. The remaining units may be derived from any other diisocyanate for example, diisocyanates in which the chain between the free valancies is provided with at least one aromatic group or more than one cycloaliphatic group, or in which the chain between the free valencies includes in combination at least one aromatic and at least one cycloaliphatic group.

Cycloaliphatic diisocyanates include for example, diisocyanates of the structure:

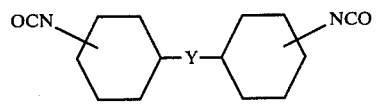

where —Y— is a divalent link which may be, for example —CH$_2$— or substituted derivative thereof, —O—, —SO$_2$—, —CO—, and the isocyanate groups are linked meta or para to the groups Y. A particular example is 4:4'-dicyclohexylmethane diisocyanate.

Aromatic diisocyanates may be included, for example 2:4- or 2:6-tolylene diisocyanates, or mixtures thereof, in which case the divalent group R$_1$ has the structure

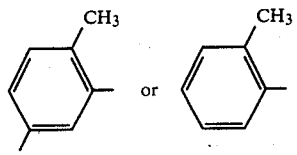

or a combination of said structures. Another suitable aromatic diisocyanate is that having the structure

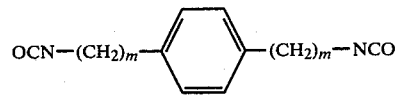

where m is a whole number chosen such that there are preferably not more than 30 atoms between cyclic groups in the urethane prepolymer derived therefrom. A suitable diisocyanate having the latter structure is xylylene diisocyanate.

Another suitable diisocyanate is that having the structure

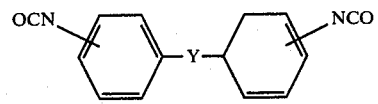

wherein Y is a divalent link which may have the designations hereinbefore described and in which the isocyanate groups are linked meta or para to the group Y. A preferred example is 4:4'-diisocyanatodiphenyl methane.

The liquid ethylenically unsaturated monomer which is reacted with the urethane prepolymer to produce the polymerisable vinyl urethane prepolymer is an ester of acrylic or methacrylic acid with a hydroxyalkanol of at least 2 carbon atoms, such an ester has the structure:

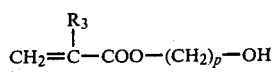

where R$_3$ is hydrogen or methyl, and p is a whole number of at least 2, or wherein one or more of the hydrogen atoms in the group —(CH$_2$)$_p$— are substituted by a hydrocarbyl group, for example, alkyl, e.g. methyl. In this case the group —X— in the polymerisable prepolymer II has the structure —COO—(CH$_2$)$_p$—O—CO—. Preferred esters are hydroxyethyl methacrylate and most preferably hydroxypropyl methacrylate including isopropyl, other isomers and mixtures thereof.

Suitable examples include hydroxy ethyl or hydroxy propyl acrylate or methacrylate made by reaction of acrylic acid or methacrylic acid with ethylene oxide or propylene oxide, in which case the group X in the polymerisable prepolymer II will have the structure

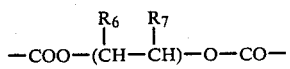

in which, respectively, both R$_6$ and R$_7$ are hydrogen, or one of R$_6$ and R$_7$ is hydrogen and the other is methyl.

The liquid ethylenically unsaturated monomer (B) is a glycol diacrylate having the formula

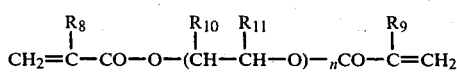

in which $R_8$ and $R_9$ are hydrogen or methyl and may be the same or different but are preferably both methyl, one of $R_{10}$ and $R_{11}$ is hydrogen and the other methyl or both are hydrogen preferably the latter, and n is an integer having value 1 to 4 inclusive.

The organic amine (C) is a reducing agent which should be capable of reducing the photosensitiser when the photosensitiser is in an excited state. The reducing agent should have little or no inhibiting effect on polymerisation. Whether or not a reducing agent has an inhibiting effect may be determined by means of simple experiment, for example, by effecting polymerisation of the polymerisable material in the composition by means of a thermal initiator alone, and in the presence of a reducing agent in the desired concentration, and comparing the rates of polymerisation in the presence of and in the absence of the reducing agent.

Suitable reducing agents include compounds having the structure

where the units R, which may be the same or different, are hydrogen atoms, hydrocarbyl groups, substituted hydrocarbyl groups or groups in which two units R together with the nitrogen atom form a cyclic ring system, no more than two of the units R being hydrogen atoms and where the nitrogen atom is attached directly to an aromatic group at least one of the groups R has a

group attached to the nitrogen atom.

The reducing agent may be a primary, secondary or tertiary amine.

One or more of the groups R may be hydrocarbyl. The hydrocarbyl group may be alkyl, cycloalkyl or araklyl. Suitably the group R may be an alkyl group having from 1 to 10 carbon atoms.

Examples of suitable reducing agents in which one or more of the units R is hydrocarbyl include propylamine, butylamine, pentylamine, hexylamine, dimethylamine, diethylamine, dipropylamine, dibutylamine, dipentylamine, trimethylamine, triethylamine, tripropylamine, tributylamine, tripentylamine, and long chain fatty amines, e.g. $C_{18}H_{37}NMe_2$. Examples of reducing agents containing aromatic groups include N,N-dimethyl aniline and N-methyl-diphenylamine.

One or more of the units R may be substituted hydrocarbyl groups and in particular the hydrocarbyl group may carry a substituent having the structure

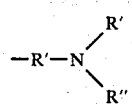

where the unit R' is, for example, an alkylene chain and the units R'', which may be the same or different, are, for example, hydrogen atoms or hydrocarbyl groups.

Examples of the reducing agents have the structure

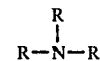

in which at least one of the units R is a substituted hydrocarbyl group include diamines of the structure

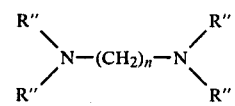

in which n is whole number of at least two and the groups R'', which may be the same or different are hydrogen atoms or hydrocarbyl, especially alkyl groups. For example, the reducing agent may be ethylene diamine, trimethylene diamine, tetramethylene diamine, pentamethylene diamine or hexamethylene diamine, or N-hydrocarbyl, especially N-alkyl derivatives thereof. Other suitable reducing agents include derivatives having the structure

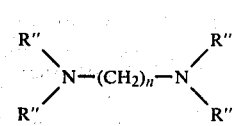

in which one or more of the hydrogen atoms in the —$CH_2$ units carry an

group, especially an —$NH_2$ group. Examples of reducing agents in which the element N forms part of a cyclic ring system include piperidine, and N-hydrocarbyl, especially N-alkyl, derivatives of piperidine.

Other reducing agents include triallylamine,

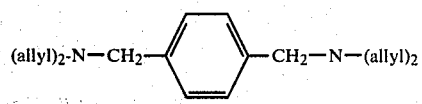

allyl thiourea and soluble salts of aromatic sulphinic acids.

A preferred reducing agent is dimethylaminoethyl methacrylate.

The concentration of organic amine in the composition is 0.25 to 0.75, preferably 0.4 to 0.6, parts by weight per hundred parts by weight of A+B. A higher concentration of amine may cause faster cure which could lead to daylight curing so increasing composition viscosity and may increase toxicity.

The α-diketone D acts as a photosensitiser for the composition and is selected from norbornane dione and substituted derivatives thereof. Norbornane has the structure

and suitable α-diketones contain the norbornane cyclic structure optionally substituted by alkyl radicals containing 1 to 10 preferably 1 to 4 carbon atoms. A preferred α-diketone which is readily available is camphorquinone which has the structure

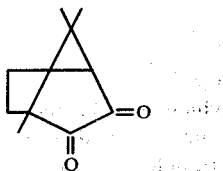

The ketone is present in the composition in concentration 0.3 to 1.0, preferably 0.5 to 1.0 and most preferably 0.65 to 0.85, parts by weight per 100 parts by weight of A+B. Higher concentration of ketone will generally cause faster cure which may lead to daylight curing so rendering the composition too viscous to use satisfactorily and so reducing chemical shelf life. Preferably the concentration of ketone is higher than that of reducing agent.

Accordingly in the present composition, the amine and the ketone act as a photosensitive catalyst for the polymerisation of the polymerisable vinyl urethane prepolymer and the liquid ethylenically unsaturated monomer. Indeed it is a feature of the present invention that low concentration of components C and D herein provide rapid cure of the selected prepolymer and monomer so leading to greater convenience in use. The compositions of the present invention are therefore cured by irradiation with visible radiation, particularly that having a wavelength in the range 400 μ to 500 μ. The radiation may be generated by conventional lamps e.g. quartz halogen, and may conveniently be directed onto the composition using fibre optics.

Whilst it is envisaged that the present composition will generally be used in the absence of filler, small quantities of filler may be included to improve for example colour, abrasion resistance. However the quantity of filler must not be so high as substantially to modify viscosity characteristics.

The filler may, for example, be in the form of spheres, platelets, fibres, whiskers or it may be irregularly shaped. Suitable fillers include, for example, apatite, soda glass, quartz, silica gel, borosilicate glass, microfine silica or synthetic sapphire (alumina). Mixtures of fillers may be used.

The polymerisable material A+B may be used together with the filler as defined above in the preparation of the liquid dental composition. Mixing of the components may be effected by stirring together the polymerisable material and filler. However the polymerisable prepolymer, optionally together with copolymerisable monomer, may conveniently be diluted with a suitable diluent so as to reduce the viscosity thus enabling adequate mixing of the filler to be more readily achieved. When mixing has been effected the diluent should be removed, e.g. by evaporation.

In order that a dental composition may be produced in which the filler adheres particularly well to the cured composition it is much preferred that the filler be treated with a coupling agent which is capable of reacting with both the filler and the components A+B before mixing of the filler and components A+B is effected. The coupling agent should have the effect of increasing the strength of the bond between the filler and the cured composition.

Because the photosensitive catalyst renders the polymerisable prepolymer and monomer sensitive to light in the 400 μ to 500 μ visible range, that part of the preparation of the present composition in which photosensitive catalyst is added should be carried out in the substantial absence of light in that range. Most conveniently, the preparation can be carried out using light outside that range for example under that emitted by sodium vapour electric discharge lamps.

Suitable coupling agents for use with glass include silanes, e.g. γ-methacryloxypropyltrimethoxysilane, γ-aminopropyltriethoxysilane and γ-glycidoxypropyltrimethoxysilane.

The composition of the present invention may be aplied to the tooth (preferably cleaned and/or acid etched) to be glazed or bonding by any suitable means, but is preferably applied by brush coating. For fissure sealant, application is preferably by dropwise addition onto the etched tooth enamel followed by self-spreading, since the procedure reduces inclusion of air bubbles and increases penetration. The coating is then cured by irradiation with visible light, preferably high intensity source directed through for example light guide onto the particular area of coating. The narrow selected range of catalyst composition enables the coating to be cured rapidly under such conditions whilst avoiding substantial cure of the composition on exposure to daylight in for example a dental surgery.

In order further to protect the present composition from partial curing in daylight it is envisaged that the composition be dispensed in containers containing small quantities (e.g. 2 g.) of the composition. In this way only small amounts are exposed to daylight during use.

The invention is illustrated with reference to the following examples. In the examples the Setting Time was determined according to British Standard 5199: 1975 (specification for Resin-based dental filling materials), paragraph 6.4. The setting was effected by exposing the sample under test to the end of Quartz optic light guide length 11 cm. diameter 8 mm. coated along its length with a Netlon sleeve (trade mark) and shrink wrap coating of polyvinyl chloride. The light source was a tungsten halogen lamp 12 volt, 75 watts (Thorn electrical Al/230).

Contact angles were determined using the following method. Clean bovine teeth were mounted in a block of dental stone and the tooth enamel polished on a lapping machine using silicon carbide paper (600 Grade —average particle size 21:8 μ) until a flat surface having diameter 1 cm. was obtained. The enamel was then etched with aqueous phosphoric acid (37% v/v phosphoric acid), washed with water and dried in air at 20° C. The prepared tooth was then mounted on an optical bench with the flat surface horizontal. A single drop of composition/formulation was applied to the flat surface using a micrometer syringe and contact angles were recorded photographically at the times specified. During the determination the composition/formulation was manipulated under yellow light from Gold fluorescent lamps (Thorn Electric, Enfield, Middlesex, England).

Viscosity of the formulation/composition was determined at 25° C. under Gold fluorescent lamp yellow light using a Haake 'Roto-Visco' viscometer.

Tensile strength was measured using flat dumbells of cured material. Dumbells were prepared having overall length 30 mm., width 5 mm. and thickness 1.75 mm. but a central neck portion length 10 mm. width 2.4 mm. (±0.2mm.). In the preparation formulation/composition was pipetted into a mould having open top and back sealed with self-adhesive tape and mould size appropriate to the required dumbell. An excess of material is used to reduce the trapping of air bubbles and when the mould was full, a layer of self-adhesive tape was used progressively to seal the open top; this sealing was effected by causing the tape to adhere to one edge of the mould and progressively pressing the tape across the open top using the straight edge of a glass slide which also acts as a squeegee to remove excess material from the mould. After sealing, the filled mould was placed on a bed moving at 16 mm/minute so that the mould passed directly beneath two lamps at a rate described hereinbefore under "setting time". Samples were removed, those containing air bubbles discarded and eight samples were used per test. Those samples were stored in de-ionised water for 24 hours at 37° C., then dried on tissue paper and allowed to equilibrate for 10 minutes at 20° C.

Load at failure (L) was measured on a Howden tensometer (type E115) and tensile strength (T) computed according to the formula:

$$T = \frac{L \times 9.81}{W \times D} \; N/mm^2$$

in which
L is load at failure (kg)
W is sample width (mm correct to 0.01 mm)
D is sample thickness (mm correct to 0.01 mm).
The tensile strength was taken as the average value after discarding those samples whose individual tensile strength was greater than 15% below the average. A minimum of 5 samples was required. Setting on the Howden tensometer were:
Load cell 50 kg
Range 50 kg
Setting Tension
Cross-head speed 5.0±0.1 mm.

Flexural Strength was measured using test-pieces prepared in a method similar to those for tensile strength but having length 3 cm. and width 2 mm, depth 2 mm. throughout their length. Load at failure (P) on a three point bend test on each test piece was measured using a Howden tensometer (type E115). Flexural strength (FS) was calculated according to the formula:

$$FS = \frac{3 \times P \times L \times 9.81}{2 \times bd^2} \; N/mm^2$$

where
P is load at failure (kg)
L is distance between tensometer supports (mm correct to 0.01 mm)
b is width of sample (mm correct to 0.01 mm)
d is depth of sample (mm correct to 0.01 mm)
Flexural strength was taken as the average value after discarding those test pieces whose individual flexural strength was more than 15% below the average. A minimum of four test results were required. Settings on the Howden tensometer were:
Load cell 50 kg
Range 5 kg
Setting Compression
Cross-Head speed 5.0±0.1 mm.

EXAMPLE 1

(a) 35.2 g. (0.1 mole) of the condensate obtained by reacting 2,2-bis-(p-hydroxyphenyl)propane and propylene oxide in a molar ratio of 1:2 (oxypropylated Bisphenol A) were dissolved in approx. 100 g. of methylene dichloride and the resulting solution was added dropwise to a solution of 33.6 g. (0.2 mole) of hexamethylene di-isocyanate in 100 g. of methylene dichloride under an atmosphere of nitrogen gas. 4 drops of dibutyl tin dilaurate (available as "Mellite" 12, "Mellite" is a registered Trade Mark) were added as catalyst. The mixture was stirred under nitrogen for 1 hour after which it was heated under reflux conditions for 9 hours. The mixture was then cooled and a solution of 29 g. (0.2 mole) of hydroxypropyl methacrylate in 100 g. of methylene dichloride was added after which the mixture was heated under reflux conditions for 3 hours. The hydroxypropyl ester comprised isomers in weight ratio 2-hydroxypropyl (2.6 parts) to 1-methyl-2-hydroxyethyl (1 part). The mixture was then cooled and the resulting polymerisable vinyl urethane prepolymer was isolated as a viscous gum by treatment of the mixture with petroleum ether followed by removal of residual solvent in a rotary evaporator.

A dental composition was prepared to the formulation:
A Vinyl urethane 13.0 g.
B Ethylene glycol dimethacrylate 10.65 g.
C Diethylamino ethyl methacrylate 0.1203 g.
D Camphorquinone 0.1775 g.
i.e.
C is a 0.51% by weight A+B
D is 0.75% by weight A+B In preparing the composition, the ethylene glycol dimethacrylate was weighed into a 250 ml. beaker containing the polymerisable vinyl urethane prepolymer. The mixture was stirred until the gum had dissolved and then the dimethylaminoethyl methacrylate and the camphorquinone were added with stirring. When the catalyst had completely dissolved, the composition was placed in a vacuum chamber in which it was degassed for approx. 2 minutes.

(b) A dental composition was prepared using the polymerisable vinyl urethane prepolymer described in (a) above except that the formulation was:
A Vinyl urethane 32.5 g.
B Triethylene glycol dimethacrylate 26.5 g.
C Dimethylaminoethyl methacrylate 0.295 g.
D Camphorquinone 0.4425 g.
i.e.
C is 0.5% by weight of A+B
D is 0.75% by weight of A+B
The components of the composition were mixed as described in (a) above.

(c) 500 g. of freshly distilled 4,4' diisocyanatodiphenyl methane were washed with 300 ml. of methylene chloride into a 5 litre flanged necked flask which had been purged with nitrogen gas. The glass was then fitted with a glass anchor stirrer, nitrogen purge, water condenser and thermometer.

352 g. of a molten condensate obtained by condensing 2,2-bis(p-hydroxydiphenyl)propane and propylene oxide, and 0.15 g. of dibutyl tin dilaurate were weighed into a 1 litre dropping funnel which had been purged with nitrogen gas. 200 ml. of methylene chloride were added to the dropping funnel to prevent the condensate from solidifying.

The dropping funnel was then placed above the flask and its contents were added dropwise to the flask over a period of 45 minutes after which the reaction was allowed to proceed for approx. 45 minutes at which time 300 g. of hydroxyethyl methacrylate were added together with 0.15 g. of dibutyl tin dilaurate over a period of 3 minutes. There was a rise in temperature of the contents of the flask and when this had subsided the flask was heated on a water bath (refluxing methylene chloride) and its contents stirred under a nitrogen purge until the infra red spectrum of the resulting product showed only a trace of isocyanate group to be present (about 3 days).

The water bath was then removed and methanol was added to the stirred contents of the flask to cause separation of the polymerisable prepolymer therein. The contents of the flask were allowed to settle and then the methanol layer was syphoned off and discarded. Washing with methanol as above was repeated several times until a clear methanol layer was obtained. The polymerisable prepolymer in the flask was then dried at room temperature under vacuum until a dry foam resulted. The foam was crushed and dried to remove traces of methanol.

A dental formulation was prepared according to the formulation:

A Vinyl urethane 53.5 g.
B Ethylene glycol dimethacrylate 43.8 g.
C Dimethylaminoethyl methacrylate 2.5 g.
D Camphorquinone 0.25 g.

i.e.

C is 2.5% by weight A+B
D is 0.25% by weight A+B

The components of the formulation were mixed as described in (a) above.

(d) A dental formulation was prepared using the vinyl urethane described in (c) above except that the formulation was:

A Vinyl urethane 34.0 g.
B Triethylene glycol dimethacrylate 27.8 g.
C Dimethylaminoethyl methacrylate 1.5446 g.
D Camphorquinone 0.1545 g.

i.e.

C is 2.5% by weight A+B
D is 0.25% by weight A+B

The components of the formulation were mixed as described in (a) above.

Each of the above four compositions and formulations were evaluated for:
1. Cure time
2. Contact angle
3. Viscosity
4. Mechanical properties of cured product.

The results of the evaluation using test procedures described below were:

|  |  | Preferred result | Composition/formulation |  |  |  |
|---|---|---|---|---|---|---|
|  |  |  | a | b | c | d |
| Setting time (seconds) |  | low | 25 | 20 | 90 | 48 |
| after | (5s) |  | 26 | 29 | 78.5 | 82 |
|  | (15s) |  | 15.5 | 19 | 56 | 60 |
|  | (25s) |  | 12 | 17 | 47 | 57 |
| Contact Angle | (35s) | low | 10.5 | 13.5 | 52 | 63.5 |
| (°) | (45s) |  | 8.5 | 13 | 48 | 49 |
| Viscosity (centipoise at 25° C.) |  | fairly low | 881 | 1224 | 9988 | 33480 |
| Tensile strength (N/mm²) |  | high | 63 | 61 | 21 | 51 |
| Flexural modulus (N/mm²) |  | high | 117 | 94 | 92 | 107 |

The results show that compositions (a) and (b) which fall inside the scope of the present invention have particularly useful preferred range of properties whilst formulations (c) and (d) which fall outside the scope of the present invention are not attractive for dental fissure sealants.

(e) A composition having the same formulation as that in (b) above but using vinyl urethane prepared in tetrahydrofuran rather than methylene chloride and prepared from ethoxylated bisphenol A had a similar setting time.

(f) A composition having the same formulation as that in (b) above but containing N,N-dimethyl aniline in place of dimethyl aminoethylmethacrylate had a setting time of 17 seconds.

EXAMPLE 2

A number of dental compositions were prepared using the vinyl urethane (A) and triethylene glycol dimethacrylate (B) and their relative concentrations of Example 1(b) but incorporating a range of levels of dimethylaminoethyl methacrylate (C) and camphorquinone (D) in order to demonstrate their effect on setting time of the compositions.

| % Weight A + B |  | Setting Time(s) |
|---|---|---|
| C | D |  |
| 0.25 | 0.75 | 25 |
| 0.40 | 0.75 | 22 |
| 0.50 | 0.75 | 20 |
| 0.75 | 0.75 | 18 |
| 1.0* | 0.75 | 16* |
| 0.5 | 0.25* | 40 |
| 0.5 | 0.50 | 30 |
| 0.5 | 1.00 | 16 |

The results show that the increasing concentrations of both amine (C) and diketone (D) reduces setting time. However further increase of diketone (D) leads to unacceptable yellowing of the composition and high concentrations (>0.75%) of amine increase composition toxicity without substantial decrease in setting time. Indeed a setting time of less than 16 seconds increases daylight sensitivity of the composition which leads to clinical handling problems and reduces shelf life of uncured resin. The compositions above which contain an asterisk opposite concentration figure for C or D fall outside the scope of the present invention.

EXAMPLE 3

For comparison purposes the concentration of dimethylaminoethyl methacrylate (C) and camphorquinone (D) in formulation 1(c) were varied to show their effect on setting time.

| % Weight A + B | | Setting Time (seconds) |
|---|---|---|
| C | D | |
| 2.50 | 0.25 | 90 |
| 2.50 | 0.50 | 70 |
| 2.50 | 0.75 | 60 |
| 2.50 | 1.00 | 50 |
| 2.50 | 2.00 | 45 |
| 2.50 | 3.00 | 45 |
| 2.50 | 4.00 | 45 |
| 2.50 | 5.00 | 55 |
| 1.5 | 0.25 | 120 |
| 0.5 | 0.25 | 200 |

The results show that even at high levels of amine (C) and diketone (D), the setting times are too high for clinical application. Additionally formulations containing ≧2.00% diketone were very yellow.

EXAMPLE 4

The dental composition described in Example 1(b) was evaluated as an orthodontic adhesive. The performance of the composition was estimated by determining tensile adhesive strength and shear bond strength of cured composition to the prepared surface of a tooth.

TENSILE ADHESIVE STRENGTH

Freshly extracted human maxillary incisors were sectioned into halves and then one half was embedded in polyester resin cylinders with the labial surface exposed at one end of the cylinder. The exposed enamel was carefully sanded flat with silicon carbide paper and water; care was taken that the surface was perpendicular to the sides of the cylinder. The enamel was then partially covered with masking tape leaving a 3 mm circle of enamel exposed. This enamel was then etched for 1 minute with 37% aqueous phosphoric acid, washed with de-ionised water for 1 minute and then dried with compressed air. A drop of dental composition was then cured onto the treated etched enamel surface; a further drop was placed on the cured drop and then cured. This procedure was repeated twice to form a dome of cured composition. Curing was effected by exposure for 30 seconds to visible radiation using the lamp and guide described under Setting Time above; the composition was about 5 mm from the end of the guide. The samples were then aged in de-ionised water at 37° C. for different periods (5 mins., 24 hours, 48 hours). The dome was attached to a second polyester resin cylinder using a further drop of dental composition which was then cured. The tensile adhesive strength was measured on the test piece using an Instron Testing Machine with cross-headed speed of 1 mm/minute. An average value for 6 samples was determined.

SHEAR BOND STRENGTH

The etched enamal surface was prepared and mounted in polyester cylinders as described above for tensile adhesive test. Each test piece was laid on its side, clamped with a vice placed on the platten of the Instron Testing Machine. A vertical steel arm with a sharp flat chisel like distal end was attached to the cross-head of the Instron. The test piece was arranged so that the chisel tip was perpendicular to the side of the cylinder and parallel to the enamel surface. The shear strength to split the attached material from the enamel surface was tested using a cross-head speed of 1 mm/minute. An average value for 6 samples was determined.

| Ageing Time in water at 37° C. | Shear Bond Strength Kg/Cm$^2$ | Tensile Adhesive Strength Kg/Cm$^2$ |
|---|---|---|
| 5 minutes | 107 | — |
| 24 hours | 136 | 125 |
| 48 hours | 130 | 109 |

The results show that the composition has excellent adhesion and shear bond strength to tooth enamel.

EXAMPLE 5

(a) A vinyl urethane was prepared as described in Example 1(a) except that polypropylene glycol (molecular weight 400) was used in place of oxypropylated Bisphenol A and that its mole ratio to hexamethylene diisocyanate reacted to produce urethane prepolymer was 9:10 and that that prepolymer was further reacted with hydroxypropyl methacrylate (2 moles). A composition according to the present invention was prepared to the formulation

| A | Vinyl urethane | 50 g |
|---|---|---|
| B | Triethylene glycol dimethacrylate | 50 g |
| C | Dimethylaminoethyl methacrylate | 0.75 g |
| D | Camphorquinone | 0.5 g | and the composition had a setting time of 25 seconds.

(b) For comparison a formulation was prepared similar to that described in (a) above but containing vinyl urethane prepared using diisocyanatodiphenyl methane in place of hexamethylene diisocyanate had a setting time of 55 seconds.

(c) For further comparison, a formulation similar to that in (a) above was prepared using tetrahydrofurfuryl methacrylate as monomer (B). This formulation had a setting time of 180 seconds.

The results given in this example show the effect of variation of diisocyanate and monomer (B) on composition setting time.

EXAMPLE 6

Two formulations were prepared both falling outside the present invention using the vinyl urethane described in Example 1 (a) to show the effect of variation in α-diketone on the setting time

| (a) | A | Vinyl urethane | 50 g |
|---|---|---|---|
| | B | Triethyleneglycol dimethacrylate | 50 g |
| | C | Dimethylaminoethyl methacrylate | 0.3 g |
| | D | Phenathraquinone | 0.3 g |
| | | Seting time in 70 seconds | |
| (b) | A | Vinyl urethane | 55 g |
| | B | Triethyleneglycol dimethacrylate | 45 g |
| | C | Dimethylaminoethyl methacrylate | 0.5 g |
| | D | Benzil | 0.95 g |
| | | (molar equivalent to 0.75 g Camphorquinone) Setting time 80 seconds | |

EXAMPLE 7

A vinyl urethane was prepared as in Example 1(a) above except that the diisocyanate used was 4,4'-dicyclohexylmethane diisocyanate. A composition was prepared having the formulation:

| | | |
|---|---|---|
| A | Vinyl urethane | 66 g |
| B | Triethyleneglycol dimethacrylate | 54 g |
| C | Dimethylaminoethyl methacrylate | 0.6 g |
| D | Camphorquinone | 0.9 g |
| | C is 0.5% by weight of A + B | |
| | D is 0.75% by weight of A + B | |

The setting time of the composition was 18 seconds.

What we claim is:

1. A liquid dental composition which comprises
(A) 50 to 55 parts by weight of polymerisable vinyl urethane prepolymer which is the reaction product of a urethane prepolymer derived from the reaction of hexamethylene diisocyanate and propoxylated bisphenol A, and hydroxypropyl methacrylate,
(B) 50 to 45 parts by weight of at least one glycol methacrylate selected from ethylene glycol dimethacrylate and triethylene glycol dimethacrylate,
(C) 0.25 to 0.75 parts by weight per 100 parts by weight A+B of dimethylaminoethyl methacrylate, and
(D) 0.5 to 1.0 parts by weight per 100 parts by weight A+B of camphorquinone.

* * * * *